United States Patent
Daniel

(10) Patent No.: US 9,012,803 B2
(45) Date of Patent: Apr. 21, 2015

(54) METHOD OF VARYING A PHYSICAL PROPERTY OF A MATERIAL THROUGH ITS DEPTH

(75) Inventor: Claus Daniel, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 762 days.

(21) Appl. No.: 13/234,779

(22) Filed: Sep. 16, 2011

(65) Prior Publication Data

US 2013/0068968 A1   Mar. 21, 2013

(51) Int. Cl.
*B23K 26/00* (2014.01)
*A61F 2/30* (2006.01)

(52) U.S. Cl.
CPC ........... *B23K 26/0084* (2013.01); *A61F 2/3094* (2013.01)

(58) Field of Classification Search
USPC .................. 219/121.69, 121.6; 250/492.1
See application file for complete search history.

(56) References Cited

U.S. PATENT DOCUMENTS

| | | | | |
|---|---|---|---|---|
| 4,608,052 | A | * | 8/1986 | Van Kampen et al. ..... 623/23.29 |
| 4,673,409 | A | * | 6/1987 | Van Kampen ............. 623/23.29 |
| 7,018,418 | B2 | | 3/2006 | Amrich et al. |
| 7,374,642 | B2 | | 5/2008 | Deutchman et al. |
| 2006/0154206 | A1 | | 7/2006 | Petersson et al. |
| 2007/0287027 | A1 | | 12/2007 | Justin et al. |
| 2008/0216926 | A1 | * | 9/2008 | Guo et al. ...................... 148/565 |
| 2009/0176034 | A1 | * | 7/2009 | Ruuttu et al. .................. 427/566 |
| 2010/0301013 | A1 | * | 12/2010 | Conneely et al. ............... 216/83 |
| 2011/0092966 | A1 | * | 4/2011 | Guo et al. ........................ 606/13 |

OTHER PUBLICATIONS

Daniel, Claus et al; Biometric Structures for Mechanical Applications by Interfering Laser Beams: More Than Solely Holographic Gratings; J. Mater. Res., vol. 21, No. 8, Aug. 2006, pp. 2098-2105.
Daniel, Claus; Bio-Mimetic Scaling of Mechanical Behavior of Thin Films, Coatings, and Surfaces by Laser Interference Metallurgy; Advanced Engineering Materials 2005, vol. 7, No. 9, pp. 823-826.
Daniel, Claus et al; Micro-Structural Characterization of Laser Interference Irradiated Ni/Al Multi-Films; Applied Surface Science 242 (2005), pp. 140-146.
Daniel, Claus et al; Laser Induced Hierarchiical Nano-Composites in Metallic Multi-Films: Structural Characterization; Functional Materials, Department for Materials Science, Saarland University, Saarbruecken, Germany.
Daniel, Claus et al; Electrical Behavior of Periodically Microstructured Sn/CuSn4 Contact Models Under Fretting Conditions; Wear 257 (2004), pp. 266-270.
Daniel, Claus et al; Stress and Texture Evolution of Ni/Al Multi-Film by Laser Interference Irradiation; Surface and Coatings Technology 180-181 (2004), pp. 478-482.

* cited by examiner

*Primary Examiner* — Dana Ross
*Assistant Examiner* — Renee L Miller
(74) *Attorney, Agent, or Firm* — Luedeka Neely Group, P.C.

(57) ABSTRACT

A method is disclosed for varying a mechanical property of a material at two depths. The method involves the application of at least two laser pulses of different durations. The method involves a determination of the density of the material from the surface to each depth, a determination of the heat capacity of the material from the surface to each depth, and a determination of the thermal conductivity of the material from the surface to each depth. Each laser pulse may affect the density, heat capacity, and thermal conductivity of the material, so it may be necessary to re-evaluate those parameters after each laser pulse and prior to the next pulse. The method may be applied to implantation materials to improve osteoblast and osteoclast activity.

13 Claims, No Drawings

METHOD OF VARYING A PHYSICAL PROPERTY OF A MATERIAL THROUGH ITS DEPTH

GOVERNMENT RIGHTS

This invention was made with government support under Contract No. DE-AC05-00OR22725 awarded by the U.S. Department of Energy. The government has certain rights in the invention.

FIELD

This disclosure relates to the field of material processing. More particularly, this disclosure relates to material processing using lasers.

BACKGROUND

Manufactured materials are often used in human and animal bone and joint replacement implantation procedures. Examples of such implants are replacement knee and hip joint components, and dental crowns and bridges. Ideally, such implants would last beyond the life expectancy of the recipient. However often the manufactured material fails in situ and a further replacement is needed. Failure of implants and the revision surgery associated with their replacement present an increasing burden to society, especially with higher life expectancies and the modern disposition to obesity. In the United States, mortality caused by hip fractures alone accounts for approximately 1% of all deaths, resulting in an estimated 33,100 life-years lost annually. In 2004, fractures accounted for 1 to 2% of total health care costs, amounting to a $20 to $40 billion burden that is projected to rise to between $40 and $80 billion in 2015. The American Academy of Orthopedic Surgeons reports an increase in partial hip replacements in the United States from 112,000 in 1998 to 240,000 in 2004. A hip replacement lasts for only about 10 to 15 years and sometimes even fails within the first year. In 2004, there were 46,000 revision hip surgeries.

Many techniques have been developed to control the bulk properties of advanced materials, such as those used in implants. Techniques have also been developed for the preparation and modification of the surface of advanced materials. However, in many applications of advanced materials the structuring of bulk properties and surface properties are inadequate to meet all of the desired characteristics of advanced materials. Examples of such circumstances are at points of interface with other materials where localized stresses may cause a material failure. What are needed therefore are techniques to modify the properties of advanced materials through a controllable depth, such as at localized points of interface with other materials

SUMMARY

The present disclosure provides a method of varying a mechanical property of a material at depths "$d_i$" and "$d_j$" by exposing a region of the material to a first laser pulse for a first pulse duration of $\tau_{p_i}$, given by $$\tau_{p_i} = \frac{d_i^2 \rho_i c_{p_i}}{4 k_{t_i}}.$$

The method further typically includes exposing the region of the material to a second laser pulse for a second pulse duration $\tau_{p_j}$ that is a different duration than the first pulse duration $\tau_{p_i}$ where $\tau_{p_j}$ is given by $$\tau_{p_j} = \frac{d_j^2 \rho_j c_{p_j}}{4 k_{t_j}}.$$

DETAILED DESCRIPTION

The following detailed description illustrates preferred and other embodiments of methods for varying a mechanical property of a material at two or more depths. It is to be understood that other embodiments may be utilized, and that structural changes may be made and processes may vary in other embodiments.

The term "implantation material" is used herein to refer to manufactured materials that are structured for implant in a human or an animal. Failures of implantation materials are often fundamentally related to cell responses to the artificial material. In the case of bones, decreasing osteoblast activity and increasing osteoclast activity lead to aseptic loosening and failure of an implant. Although great bone implant improvements have been made using coatings, porous materials, and cementing fixation, implant lifetimes are still not adequate.

Stress shielding has been identified as a major reason for implant loosening. Due to the far higher stiffness of the implant compared to the natural bone material, there is a step function of stiffness and no force transfer from the implant to the bone. Thus, the stress to the bone is shielded by the implant, and osteoblast activity is minimized. A porous metal, such as a metal foam, seems to be the most promising material for improved implants. Improved fixation can be achieved by bone tissue growing into and through the porous metal matrix and locking the implant to the host bone. Another valuable property of this method is the low stiffness of the porous metal compared with that of fully dense metal. The stiffness may be engineered to differing extents by the degree of porosity. Although the resulting "macroscopic" mechanical properties can be designed to almost match bone-like behavior, the microscopic properties remain the same as that of bulk material. Since many surface pores each have a pore diameter that is generally in a range from 50 to 200 μm, it means that microscopically there is still a stiffness mismatch and resulting stress shielding. Therefore, osteoblast activity and bone in-growth are still highly limited. The porous metal also shows stress concentrations at points of singularity, such as pore walls or wall connections. These singularities provide weak points for crack initiation, leading to a catastrophic failure of the material.

Coated and foam surfaces may be restructured and strengthened, and cell-surface interaction may be controlled on the micro-scale by using a laser direct structuring technique. Multiple coherent high-power short-pulses of laser beams may used to produce an ultrafast periodic heat treatment on the implant surface, creating three dimensional effects. Such techniques typically do not require special environments or vacuum conditions. Additionally, this technique is insensitive to topographic changes of up to several millimeters, which makes it generally suitable as a treatment for materials having a powder metal surface (such as provided by a powdered metal coating) and for porous metals (such as metal foams).

With present laser systems, the surface treatment area may typically be an area of 27 mm². With future laser systems of higher power and larger beams, this capability is expected to increase dramatically. With current systems a single laser pulse may generate temperature gradients of more than 1,500° C. on submicrometer distances with only about 200 ns needed to return the material to room temperature. Such elevated temperatures, even for such short durations, are sufficient to modify the physical properties of a material.

A basic process embodiment utilizes two laser pulses of different durations applied to the same surface region of a material. The duration of the pulses depends on the following factors:
1) the depth d to which material modification is desired;
2) the density $\rho$ of the material from the surface to the depth d;
3) the heat capacity $c_p$ of the material from the surface to the depth d; and
4) the thermal conductivity $k_t$ of the material from the surface to the depth d.

The duration of a first pulse of laser energy $\tau_{p_i}$ is given by Equation 1.

$$\tau_{p_i} = \frac{d_i^2 \rho_i c_{p_i}}{4k_{t_i}} \quad \text{(Eq'n 1)}$$

where the i subscript denotes the respective material property of the $i^{th}$ pulse (i.e., the first pulse in this case.

Note that the distance d is a thermal diffusion length, which is the distance from a surface (heated by a laser heat source) in which the temperature is reduced to the 1/e of the initial temperature at the surface. This distance is relative to the absorbed and thermalized energy provided by a laser pulse. Hence the temperature at the surface of the material generated by the laser pulse is used to calculate the depth d to which material modification will occur. Different pulse durations will produce different surface temperatures, so a reiterative calculation is generally needed to arrive at the desired temperature at the depth d, and hence to arrive at $\tau_{p_i}$.

The material is then subjected to at least one further pulse of duration $\tau_{p_j}$ that is different from duration $\tau_{p_i}$. The duration of the second pulse $\tau_{p_j}$ is given by Equation 2:

$$\tau_{p_j} = \frac{d_j^2 \rho_j c_{p_j}}{4k_{t_j}} \quad \text{(Eq'n 2)}$$

The material properties $\rho_j$, $c_{p\,j}$, and $k_{t\,j}$, may be altered by the effects of the first pulse, and consequently may need measured after the first pulse. That is, $\tau_{p_i}$ and $\tau_{p_j}$ may calculated using different values for $\rho_i$ and $\rho_j$, and/or different values for $c_{pi}$ and $c_{pj}$, and/or different values for $k_{ti}$ and $k_{tj}$.

The measurements of $\rho_j$, $c_{pj}$, $k_{tj}$ and may require destruction of one or more samples created with the first pulse, and multiple iterations may be needed to arrive at the appropriate values for $\tau_{p_i}$ and $\tau_{p_j}$. However, such iterations will result in time durations that then may be used for production of an extensive number of articles with the desired properties at depths "$d_i$" and "$d_j$."

It is often beneficial to apply the pulses in durations that successively decrease in duration. That is, if two pulses are used, it is often beneficial to have the first pulse duration longer than the second pulse duration. The reason for this is that the longer pulse may be timed to have a greater thermal diffusion length than the second pulse. Thus the second pulse will not appreciably affect the thermal properties already modified by the first pulse.

These treatments change the mechanical properties in gradient microstructures. The microstructures do not show singularities or weak interfaces and are therefore better able to transfer force to the bone structure, resulting in increased osteoblast activity. The increased osteoblast activity leads to better osseointegration, thus extending implant longevity.

In summary, embodiments disclosed herein provide methods varying a mechanical property of a material at depths at two or more depths, such as "$d_i$" and "$d_j$." The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A method of varying a mechanical property of a material at different depths "$d_i$" and "$d_j$" from a surface of the material, the method comprising:
determining a duration $\tau_{p_i}$ given by of a first laser pulse according to:

$$\tau_{p_i} = \frac{d_i^2 \rho_i c_{pi}}{4k_{ti}},$$

where $\rho_i$ is a density of the material between the surface of the material and the depth $d_i$ prior to exposure of the material to the first laser pulse, $c_{pi}$ is a heat capacity of the material between the surface of the material and the depth $d_i$ prior to exposure of the material to the first laser pulse, and $k_{ti}$ is a thermal conductivity of the material between the surface of the material and the depth $d_i$ prior to exposure of the material to the first laser pulse;

exposing a region of the material to the first laser pulse for the duration $\tau_{p_i}$;

determining a duration $\tau_{p_j}$ second laser pulse that is a different duration than the duration $\tau_{p_i}$ of the first laser pulse according to:

$$\tau_{p_j} = \frac{d_j^2 \rho_j c_{pj}}{4k_{tj}},$$

where $\rho_j$ is a density of the material between the surface of the material and the depth $d_j$ after exposure of the region of the material to the first laser pulse, $c_{pj}$ is a heat capacity of the material between the surface of the material and the depth $d_j$ after exposure of the region of the material to the first laser pulse, and $k_{tj}$ is a thermal conductivity of the material between the surface of the material and the depth $d_j$ after exposure of the region of the material to the first laser pulse; and exposing the region of the material to the second laser pulse for the duration $\tau_{p_j}$.

2. The method of claim 1 wherein the duration $\tau_{p_i}$ is greater than the duration $\tau_{p_j}$.

3. The method of claim 1 wherein $\tau_i$ is not equal to $\rho_j$.

4. The method of claim 1 wherein $c_{pi}$ is not equal to $c_{pj}$.

5. The method of claim 1 wherein $k_{ti}$ is not equal to $k_{tj}$.

6. The method of claim 1 wherein the material is an implantation material.

7. The method of claim 1 wherein the material has surface pores with each pore having a pore diameter that is within a range between 50 μm and 200 μm.

8. The method of claim 1 wherein the material is an implantation material having surface pores with each pore having a pore diameter that is within a range between 50 μm and 200 μm.

9. The method of claim 1 wherein the material has a powdered metal surface.

10. The method of claim 1 wherein the material is an implantation material having a powdered metal surface.

11. The method of claim 1 further comprising, prior to determining the duration $\tau_{p_j}$, determining the values of $\rho_j$, $c_{pj}$, and $k_{tj}$ based on measurements performed on a sample of the material exposed to a laser pulse of duration $\tau_{p_i}$.

12. A method of heat treating a medical implant article comprising a medical implant material, the method comprising:
(a) exposing a surface of a sample of the medical implant material to a laser pulse having a first duration $\tau_{p_i}$ over an exposed region to create a temperature gradient in the sample of the medical implant material to a depth $d_i$ below the surface within an exposed region;
(b) measuring properties of the sample of the medical implant material within the exposed region after exposure to the laser pulse, the properties including one or more of a density $\rho_j$ of the medical implant material within the exposed region, a heat capacity $c_{pj}$ of the medical implant material within the exposed region, and a thermal conductivity $k_{tj}$ of the medical implant material within the exposed region;
(c) calculating a second duration $\tau_{p_j}$ based at least in part on the properties of the sample of the medical implant material measured in step (b);
(d) exposing a surface of the medical implant article to a laser pulse having the first duration $\tau_{p_i}$ over an exposed region of the medical implant article to create a first temperature gradient in the medical implant article to the depth $d_i$ below the surface within an exposed region; and
(e) exposing the surface of the medical implant article to a laser pulse having the second duration $\tau_{p_j}$ over the exposed region of the medical implant article to create a second temperature gradient in the medical implant article to a depth $d_j$ below the surface within the exposed region.

13. The method of claim 12 wherein step (c) comprises calculating the second duration $\tau_{p_j}$ according to $$\tau_{p_j} = \frac{d_j^2 \rho_j c_{pj}}{4 k_{tj}}.$$

* * * * *